(12) United States Patent
Savidakis et al.

(10) Patent No.: US 6,211,399 B1
(45) Date of Patent: **\*Apr. 3, 2001**

(54) PRESSURIZED CHLORINATION AND BROMINATION OF AROMATIC COMPOUNDS

(75) Inventors: Michael C. Savidakis, Niagara Falls; David C. Johnson, Cheektowaga, both of NY (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/412,672

(22) Filed: Oct. 5, 1999

(51) Int. Cl.⁷ .......................... C07C 69/76; C07C 255/00; C07C 17/00; C07C 45/00
(52) U.S. Cl. .......................... 560/103; 558/425; 568/323; 568/656; 570/206; 570/207; 570/210
(58) Field of Search ........................... 560/103; 558/425; 568/323, 656; 570/206, 207, 210

(56) References Cited

U.S. PATENT DOCUMENTS

| | | | |
|---|---|---|---|
| 3,000,975 | 9/1961 | Di Bella | 260/650 |
| 3,366,698 | 1/1968 | Di Bella | 260/650 |
| 4,013,730 * | 3/1977 | Graham | 260/650 R |
| 4,794,201 | 12/1988 | Higuchi et al. | 570/208 |
| 4,835,327 | 5/1989 | Milam et al. | 570/208 |
| 4,925,994 * | 5/1990 | Mais et al. | 570/210 |

\* cited by examiner

*Primary Examiner*—Sreeni Padmanabhan
(74) *Attorney, Agent, or Firm*—Richard D. Fuerlle; Anne E. Brookes

(57) ABSTRACT

Disclosed is a method of adding 1 to 4 chlorine or bromine atoms to an aromatic ring of compound that has at least one electron-withdrawing groups on that ring. The aromatic compound is reacted with a chlorinating agent or a brominating agent in the presence of about 0.1 to about 10 mole % of a Lewis acid catalyst at a temperature of ambient to about 100° C. and a pressure of about 10 to about 100 psig.

20 Claims, No Drawings

PRESSURIZED CHLORINATION AND BROMINATION OF AROMATIC COMPOUNDS

BACKGROUND OF THE INVENTION

This invention relates to a method of chlorinating and brominating aromatic compounds. In particular, it relates to a method of chlorinating and brominating aromatic compounds under pressure using only a catalytic amount of a Lewis acid catalyst.

Aromatic compounds, such as methyl4methylbenzoate (M4MB), are commonly chlorinated at atmospheric pressure using chlorine gas in the presence of a Lewis acid catalyst, such as aluminum chloride, $AlCl_3$, or ferric chloride, $FeCl_3$. The amount of Lewis acid catalyst used must be greater than stoichiometric to effect the chlorination. For example, 0.98 lbs. (1.1 equivalents) of aluminum chloride are required to chlorinate each pound of M4MB.

After the reaction is complete, separation of the catalyst from the product by filtration or distillation is impractical or not possible because the catalyst is chemically bound to the product. The usual procedure is to add water, causing the catalyst to react with the water to form a soluble product. For example, an aluminum chloride catalyst reacts with water to form hydrochloric acid and aluminum hydroxide, which dissolve in the water and can be separated from the solid product.

SUMMARY OF THE INVENTION

We have discovered that if an aromatic compound is chlorinated or brominated under pressure it is not necessary to use a stoichiometric amount of a Lewis acid catalyst, and that the reaction will proceed using only a catalytic amount. As a result, we can drastically reduce the amount of catalyst used, which reduces the amount of waste that must be processed and disposed of. Also, the material is easier to process when much less catalyst is present.

The work-up with water is also eliminated. Instead, the catalyst can be removed by filtration, using a filter material with an affinity for the catalyst, a procedure that is not practical when a stoichiometric amount of catalyst is used. Alternatively, the product mixture can be distilled, which separates the desired product from the complex of the catalyst and product. Only a small amount of product is lost, compared to the large amounts of product lost if a stoichiometric amount of catalyst is used.

DESCRIPTION OF THE EMBODIMENTS

The substrates to be chlorinated or brominated can be any compound having an aromatic ring with at least one site available (i.e., a hydrogen atom) and at least one electron-withdrawing group on that ring. Preferably, the compound has 1 to 3 cojoined aromatic rings with 1 or 2 electron-withdrawing groups on each ring to be chlorinated; more electron-withdrawing groups on a ring may deactivate the ring and require more rigorous conditions. Types of aromatic compounds that can be used include benzoates, benzotrihalides, halogenated aromatics, acetophenones, and benzophenones; benzoates are preferred as they are economically important. Preferred aromatic compounds have the general formula

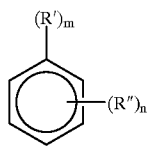

where each R' is an electron-withdrawing group independently selected from carboxylate, keto, trihalomethyl, and nitrilo, each R" is independently selected from R and OR, R is alkyl from $C_1$ to $C_{18}$, m is 1 or 2, and n is 0 to 5–m. Preferably, R' is ester, R" is R, R is alkyl from $C_1$ to $C_6$, m is 1, and n is 1 as those compounds are more important. Examples of particular aromatic compounds that can be chlorinated or brominated using this invention include methyl-4-methylbenzoate, methyl-3-methylbenzoate, methyl-3-chloro-4-methylbenzoate, p-chlorobenzonitrile, benzotrifluoride, parachlorobenzotrifluoride, benzotrichloride, parachlorobenzotrichloride, 2-chloronaphthalene, and 3'-chloroanthracene.

Any Lewis acid catalyst can be used, including aluminum chloride, ferric chloride, antimony (III) chloride, lead (IV) chloride, molybdenum (VI) chloride, thallium (I) chloride, tin (IV) chloride, titanium (IV) chloride, tungsten (VI) chloride, zirconium (IV) chloride, and mixtures thereof. The preferred Lewis acid catalyst is ferric chloride as it is inexpensive, easily removed from the product mixture, and environmentally friendly. About 0.1 to about 10 mole % (based on the aromatic compound) of the Lewis acid catalyst can be used; less is less effective and requires a long reaction time and more is unnecessary and offers no additional advantage. The preferred amount of Lewis acid catalyst is about 0.5 to about 5 mole %.

Examples of chlorinating and brominating agents include chlorine gas, liquid bromine, BrCl, $So_2Cl_2$, $SOCl_2$, $COCl_2$, $C_2O_2Cl_4$, $C_3O_3Cl_6$, n-chlorosuccinimide, n-bromosuccinimide, and 1,3-dibromo-5,5-dimethylhydantoin. Preferably, the chlorinating agent is chlorine gas and the brominating agent is liquid bromine as they effective and easier to use. About 1 to about 3 equivalents of chlorinating agent or brominating agent should be used for each chlorine or bromine atom to be added to the aromatic ring. Chlorination is preferred to bromination as it is commercially more important.

It is preferable to perform the reaction without a solvent in order to maximize throughput. However, if the desired product is a solid, it may be desirable to use about 5 to about 50 wt % of a solvent such as methylene chloride, chloroform, or dichloroethane to facilitate separation of the product.

The reaction can be performed at a temperature from about ambient to about 100° C.; at lower temperatures the reaction is slower and at higher temperatures byproducts may form. The preferred temperature range is about 40 to about 75° C.

The general procedure for the reaction is to charge a pressure reactor (i.e., an autoclave) with all the substrate, all the catalyst, and some of the chlorinating agent or brominating agent and heat the mixture. As the reaction proceeds, the pressure is maintained by pressure relief system valves. Additional chlorinating or brominating agent is added as needed. To complete the reaction, the pressure should rise to about 10 to about 100 psig (about 69 to about 690 KPa) as less pressure is ineffective and higher pressures are unnecessary and require specialized equipment; the maximum pressure is preferably about 20 to about 75 psig (about 138 to about 518 KPa). The products can be separated by distillation, filtration, or other means. The chlorinated and brominated aromatics can be used as chemical intermediates to make pharmaceuticals, agricultural chemicals, and other products.

The following examples further illustrated this invention:

EXAMPLES 1 to 3

A 300 mL L autoclave was charged with 150 g M4MB and various amounts of ferric chloride and pressurized with chlorine gas. Additional chlorine was added as needed and the pressure was maintained using a pressure relief valve. The following table gives the conditions used and the results:

| Example | 1* | 2 | 3 |
|---|---|---|---|
| FeCl$_3$ (mole %) | 9.93 | 3.03 | 1.02 |
| Temperature (° C.) | 51 to 67 | 51 to 67 | 50 to 67 |
| Pressure (psig) | 50 to 70 | 66 to 73 | 58 to 75 |
| Cl$_2$ (equivalents) | 8.11 | 9.41 | 7.11 |
| CO$_2$CH$_3$ / Cl / CH$_3$ | 71.6 | 5.8 | 68.3 |
| CO$_2$CH$_3$ / Cl, Cl / CH$_3$ | 14.3 | 38.7 | 15.7 |
| CO$_2$CH$_3$ / Cl, Cl / CH$_3$ | 8.5 | 18.5 | 9.4 |
| CO$_2$CH$_3$ / Cl, Cl / CH$_3$ | 3.1 | 2.8 | 3.3 |
| CO$_2$CH$_3$ / Cl, Cl, Cl / CH$_3$ | 1.3 | 31.9 | 1.2 |
| Other | 1.2 | 3.2 | 2.1 |

*Ester demethylation occurred

These examples show that M4MB can be effectively chlorinated under pressure using catalytic amounts of a Lewis acid catalyst.

We claim:

1. A method of adding 1 to 4 chlorine or bromine atoms to the aromatic ring of a compound having at least one electron-withdrawing group on said ring comprising reacting said compound with a chlorinating agent or a brominating agent in the presence of about 0.1 to about 10 mole % of a Lewis acid catalyst at a temperature of ambient to about 100° C. and a pressure of about 10 to about 100 psig.

2. A method according to claim 1 wherein said compound has a single aromatic ring.

3. A method according to claim 1 wherein said compound has 1 or 2 electron-withdrawing groups on said aromatic ring.

4. A method according to claim 1 wherein said electron-withdrawing group is a keto group.

5. A method according to claim 1 wherein said electron-withdrawing group is a nitrilo group.

6. A method according to claim 1 wherein said electron-withdrawing group is a carboxylate group.

7. A method according to claim 1 wherein said electron-withdrawing group is a trihalomethyl group.

8. A method according to claim 1 wherein said compound is a benzoate.

9. A method according to claim 8 wherein said benzoate is methyl-4-methyl benzoate.

10. A method according to claim 1 wherein said Lewis acid is ferric chloride.

11. A method according to claim 1 wherein a chlorinating agent is used in said reaction.

12. A method according to claim 11 wherein said chlorinating agent is chlorine gas.

13. A method according to claim 1 wherein the amount of said chlorine gas is about 1 to about 3 equivalents per chlorine atom to be added to said aromatic ring.

14. A method according to claim 1 wherein said pressure is about 20 to about 75 psig.

15. A method according to claim 1 including the additional last step of passing the product mixture through a filter that has an affinity for said Lewis acid catalyst.

16. A method of adding 1 to 3 chlorine atoms to the ring of a compound having the general formula

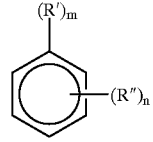

comprising (A) charging an autoclave with said compound and about 0.5 to about 5 mole % of a Lewis acid; and (B) adding about 1 to about 3 equivalents of chlorine gas to said reactor per chlorine atom to be added to said ring; and (C) heating said reactor to a temperature of about 40 to about 75° C. and a pressure of about 20 to about 75 psig, where each R' is independently selected from an carboxylate, keto, trihalomethyl, and nitrilo, each R" is independently selected from R or OR, R is alkyl from C$_1$ to C$_6$, m is 1 or 2, and n is 0 to 5–m.

17. A method according to claim 16 wherein said Lewis acid is ferric chloride.

18. A method according to claim 16 wherein R' is carboxylate.

19. A method according to claim 18 wherein said compound is a benzoate.

20. A method of adding 1 to 3 chlorine atoms to the aromatic ring of methyl-4-methylbenzoate comprising
(A) placing in an autoclave
(1) methyl-4-methylbenzoate;
(2) about 0.5 to about 5 mole % ferric chloride; and
(3) about 1 to about 3 equivalents of chlorine gas per chlorine atom to be added to the ring of said aromatic ring; and
(B) heating said autoclave to a temperature of about 40 to about 75° C. and a pressure of about 20 to about 75 psig.

* * * * *